(12) United States Patent
Tomiyama et al.

(10) Patent No.: US 7,795,229 B2
(45) Date of Patent: Sep. 14, 2010

(54) SERUM CHOLESTEROL LOWERING AGENT OR PREVENTATIVE OR THERAPEUTIC AGENT FOR ATHEROSCLEROSIS

(75) Inventors: Hiroshi Tomiyama, Nagano (JP); Masayuki Yokota, Nagano (JP); Kazuhiro Kosakai, Nagano (JP)

(73) Assignee: Kotobuki Pharmaceutical Co., Ltd. (JP)

( * ) Notice: Subject to any disclaimer, the term of this patent is extended or adjusted under 35 U.S.C. 154(b) by 169 days.

(21) Appl. No.: 10/560,357

(22) PCT Filed: Jun. 15, 2004

(86) PCT No.: PCT/JP2004/008678

§ 371 (c)(1),
(2), (4) Date: Dec. 12, 2005

(87) PCT Pub. No.: WO2005/000353

PCT Pub. Date: Jan. 6, 2005

(65) Prior Publication Data
US 2006/0154876 A1    Jul. 13, 2006

(30) Foreign Application Priority Data
Jun. 27, 2003    (JP) .............................. 2003-185171

(51) Int. Cl.
A61K 31/70    (2006.01)
A01N 43/04    (2006.01)
(52) U.S. Cl. ....................................... 514/25
(58) Field of Classification Search ........................ None
See application file for complete search history.

(56) References Cited

U.S. PATENT DOCUMENTS

| 5,661,145 A * | 8/1997 | Davis | 514/210.02 |
| 5,756,470 A * | 5/1998 | Yumibe et al. | 514/25 |
| 7,045,515 B2 * | 5/2006 | Tomiyama et al. | 514/210.02 |
| 2004/0063929 A1 | 4/2004 | Tomiyama et al. | |

FOREIGN PATENT DOCUMENTS

| WO | WO 94/14433 | 7/1994 |
| WO | WO 95/26334 | 10/1995 |
| WO | WO 97/16455 | 5/1997 |
| WO | WO 02/50090 | 6/2002 |
| WO | WO 02/058732 | 8/2002 |
| WO | WO 02/066464 | 8/2002 |

OTHER PUBLICATIONS

Bellosta et al. Circulation 2004; 109;III-50-III-57.*

Zetia: Prescribing Information [Online]. MERCK/Schering-Plough Pharmaceuticals, 2001, 2002 [Retrieved from the interenet: URL: http://www.drugs.com/PDR/zetia_tablets.html.

Zetia Tablets Professional Drug Information, published Mar. 2003, Rev. 01, URL: http://www.zetia.com/zetia/shared/documents/zetia_pi.pdf (published in Mar. 2005, Rev 07.

* cited by examiner

Primary Examiner—Shaojia Anna Jiang
Assistant Examiner—Layla Bland
(74) Attorney, Agent, or Firm—H. Jay Spiegel; Robert L. Haines

(57) ABSTRACT

A serum cholesterol lowing agent or a preventive or therapeutile agent for atherosclerosis, which each comprises a combination of a compound represented by the following general formula (I) or pharmaceutical acceptable salts thereof with a cholesterol biosynthesis inhibitor and/or a fibrate type cholesterol lowering agent. (I) (b) (a) [In the formula, $A_1, A_2, A_3$ and $A_4$ each is hydrogen, a group represented by the formula (b), or a group represented by the formula (a), provided that at least one of these is a group represented by the formula (a); $A_2$ is $C_{1-5}$ alkyl etc; and n. p, q and r each is an integer of 0, 1 or 2.

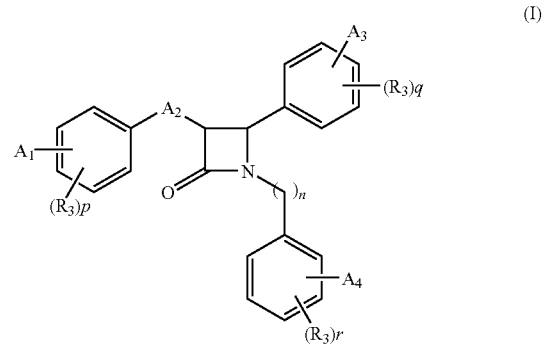

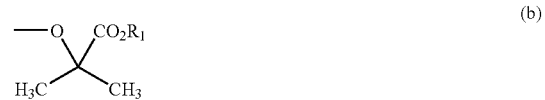

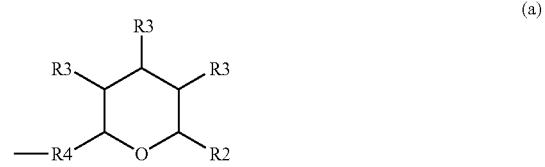

4 Claims, No Drawings

SERUM CHOLESTEROL LOWERING AGENT OR PREVENTATIVE OR THERAPEUTIC AGENT FOR ATHEROSCLEROSIS

FIELD OF THE INVENTION

The present invention relates to medicinal compositions that are useful as serum cholesterol lowering agent or preventive or therapeutic agent for atherosclerosis, in more detail, relates to medicinal compositions of β-lactam cholesterol absorption inhibitors containing C-glycoside in those molecules combined with cholesterol biosynthesis inhibitors and/or fibrate-type cholesterol lowering agents.

BACKGROUND OF THE INVENTION

Conventionally, cholesterol biosynthesis inhibitors or fibrate-type cholesterol lowering agents have been widely used for serum cholesterol reduction and prevention or therapy of atherosclerosis, and proposing the combination of β-lactam cholesterol absorption inhibitors and cholesterol biosynthesis inhibitors (JP 8-505141). The present applicant has previously published that β-lactam cholesterol absorption inhibitors containing C-glycoside in those molecules have an excellent cholesterol lowering action, and are useful as serum cholesterol lowering agents (WO-02/066464 A1).

The purpose of the present invention is supply of more excellent serum cholesterol lowering agent or preventive or therapeutic agent for atherosclerosis.

DISCLOSURE OF THE INVENTION

The present invention is serum cholesterol lowering agent or preventive or therapeutic agent for atherosclerosis consist of the combination of a compound represented by the following general formula (I) or pharmaceutical acceptable salts and cholesterol biosynthesis inhibitors and/or fibrate-type cholesterol lowering agents.

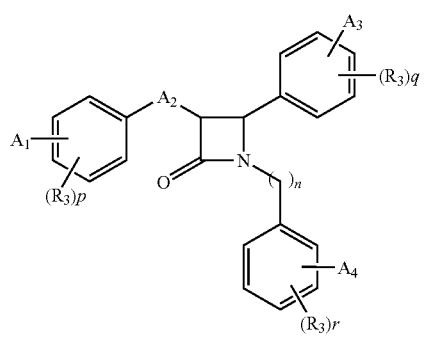

(I)

[wherein: $A_1$, $A_3$ and $A_4$ are hydrogen atom, halogen atom, alkyl group having one to five carbon atoms, alkoxy group having one to five carbon atoms, —COOR$_1$, a following formula:

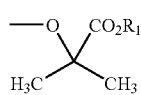

(b)

(wherein: $R_1$ is hydrogen atom or alkyl group having one to five carbon atoms) or a following formula:

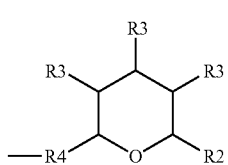

(a)

[wherein: $R_2$ is —CH$_2$OH group, —CH$_2$OC(O)—R$_1$ group or —CO$_2$—R$_1$ group; $R_3$ is —OH group or —OC(O)—R$_1$ group; $R_4$ is —(CH$_2$)$_k$R$_5$(CH$_2$)$_l$— (k and l are 0 or 1 more integer; k+l is 10 or fewer integer) and binds to tetrahydropyran ring by C—C bond. $R_5$ means single bond (—), —CH=CH—, —OCH$_2$—, carbonyl group or —CH(OH)—.] More than one of $A_1$, $A_3$ and $A_4$ in formula (I) must be the group in above-mentioned formula (a). $A_2$ is alkyl chain having one to five carbon atoms, alkoxy chain having one to five carbon atoms, alkenyl chain having one to five carbon atoms, hydroxyl alkyl chain having one to five carbon atoms or carbonyl alkyl chain having one to five carbon atoms. n, p, q or r are 0, 1 or 2.]

Also, the present invention is serum cholesterol lowering agent or preventive or therapeutic agent for atherosclerosis consist of the mixture of a compound represented by the above general formula (I) or pharmaceutical acceptable salts and cholesterol biosynthesis inhibitors and/or fibrate-type cholesterol lowering agents. Also, the present invention is serum cholesterol lowering agent or preventive or therapeutic agent for atherosclerosis formed a kit by single packaging a container containing a compound represented by the above general formula (I) or pharmaceutical acceptable salts and a container containing cholesterol biosynthesis inhibitor and/or fibrate-type cholesterol lowering agents. Also, it is able to administer a compound represented by the above general formula(I) or pharmaceutical acceptable salts and cholesterol biosynthesis inhibitors and/or fibrate-type cholesterol lowering agents simultaneously or consecutively.

PREFERRED EMBODIMENT OF THE INVENTION

The present invention is serum cholesterol lowering agent or preventive or therapeutic agent for atherosclerosis consisting of the combination of a compound represented by the following general formula (I) or pharmaceutical acceptable salts and cholesterol biosynthesis inhibitors and/or fibrate-type cholesterol lowering agents. Concretely, this combined medicine means: ① the medicine combined a compound represented by the general formula (I) or pharmaceutical acceptable salts with cholesterol biosynthesis inhibitors, ② the medicine combined a compound represented by the general formula (I) or pharmaceutical acceptable salts with fibrate-type cholesterol lowering agents, ③ the medicine combined a compound represented by the general formula (I) or pharmaceutical acceptable salts with cholesterol biosynthesis inhibitors and fibrate-type cholesterol lowering agents. This combined usage means combined administration, and is able to administer simultaneously or consecutively.

A compound represented by the above general formula (I) or pharmaceutical acceptable salts in the present invention have serum cholesterol lowering actions. These compounds are shown in WO-02/066464 A1. These β-lactam compounds, which show cholesterol lowering actions and has C-glycoside in those molecules, show synergistic effects by using in combination with cholesterol biosynthesis inhibitors and/or fibrate-type cholesterol lowering agents for serum cholesterol lowering effect or preventive or therapeutic effect for atherosclerosis.

A compound represented by the above general formula (I) or pharmaceutical acceptable salts using in the present invention are, for example, the compounds shown in Table 1~12.

TABLE 1

| No. | Structure | mp (° C.) | $[\alpha]_D^{25}$/(C, Solv.) |
|---|---|---|---|
| 1 | 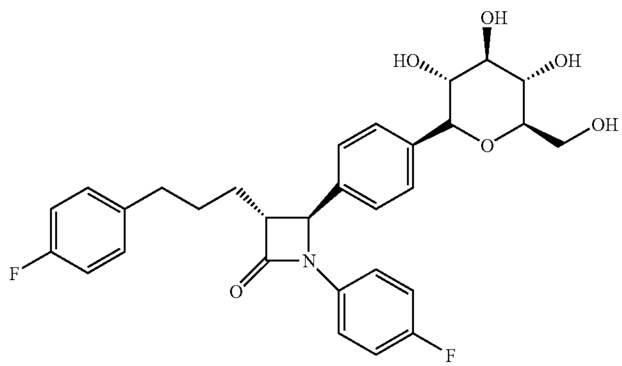 | 89-90 | −40.4 (C = 0.5, MeOH) |
| 2 | 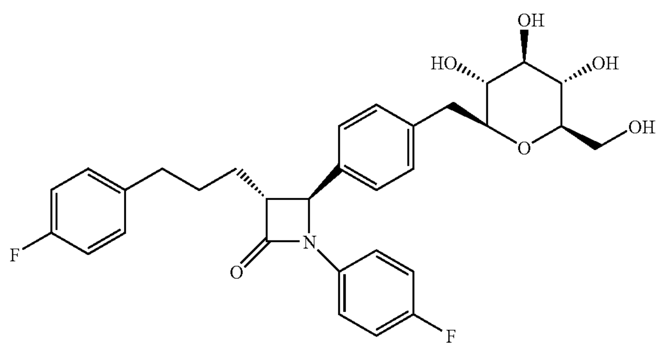 | 110-112 | −33.2 (C = 0.5, MeOH) |
| 3 | 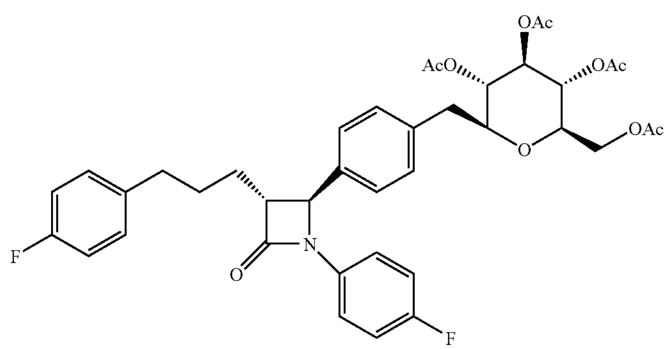 | 56-58 | |
| 4 | 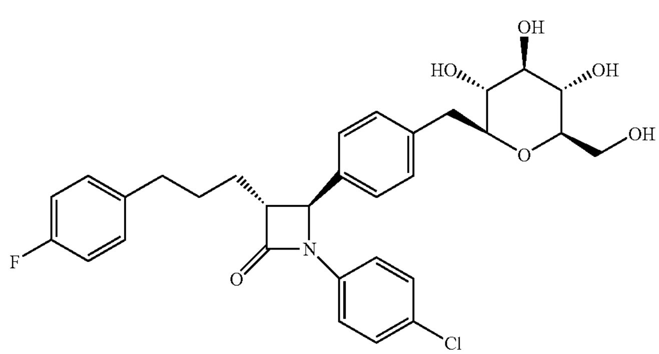 | 76-78 | |

TABLE 1-continued

| No. | Structure | mp (° C.) | $[\alpha]_D^{25}$/(C, Solv.) |
|---|---|---|---|
| 5 | 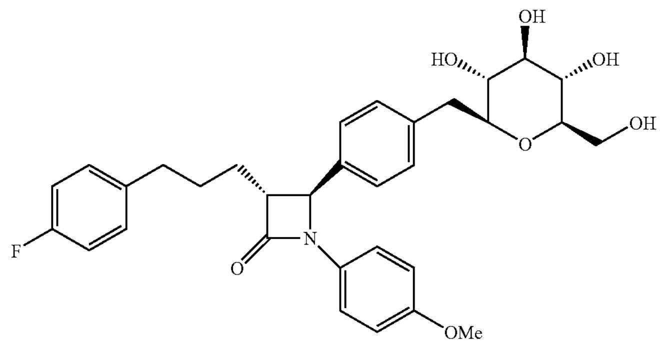 | 73-75 | |

TABLE 2

| No. | Structure | mp (° C.) | $[\alpha]_D^{25}$/(C, Solv.) |
|---|---|---|---|
| 6 | 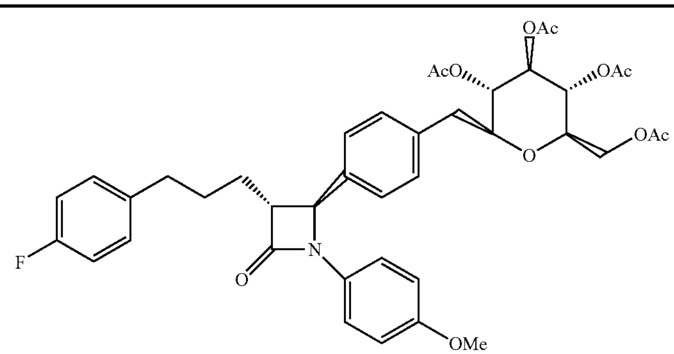 | 60-62 | |
| 7 | 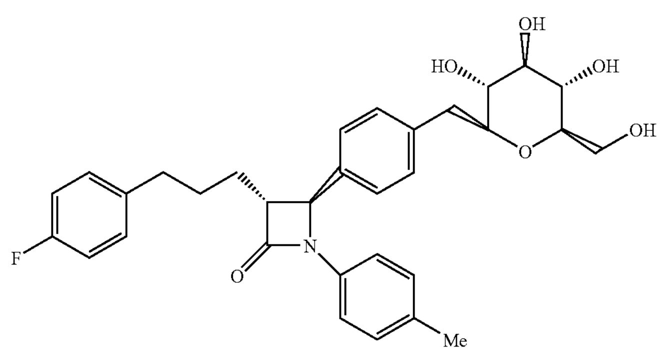 | 80-82 | −46.7 (C = 0.3, MeOH) |
| 8 | 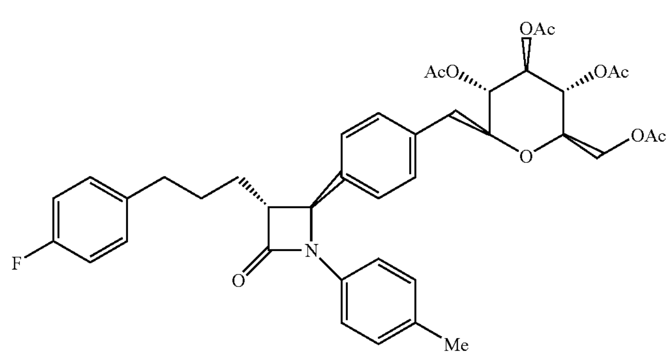 | 56-58 | |

TABLE 2-continued

| No. | Structure | mp (° C.) | $[\alpha]_D^{25}$/(C, Solv.) |
|---|---|---|---|
| 9 | 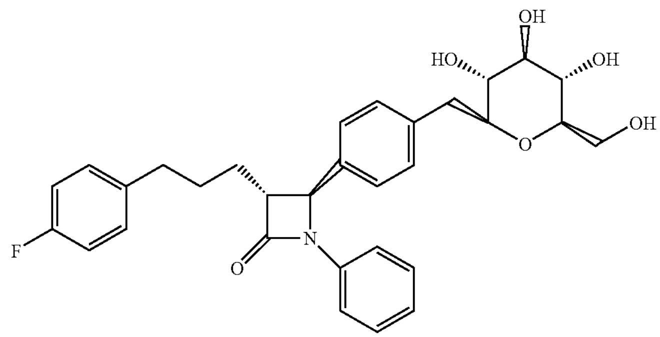 | 84-86 | −40.4 (C = 0.5, MeOH) |
| 10 | 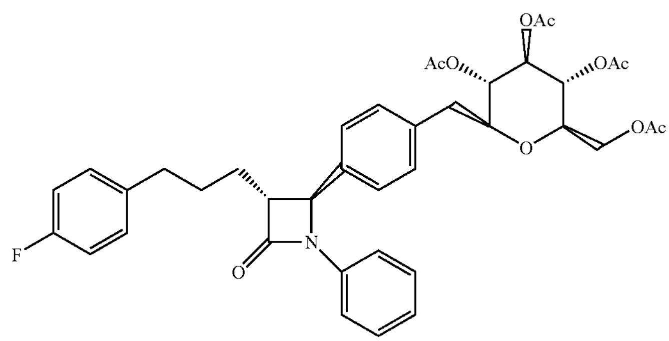 | 60-61 | |

TABLE 3

| No. | Structure | mp (° C.) | $[\alpha]_D^{25}$/(C, Solv.) |
|---|---|---|---|
| 11 | 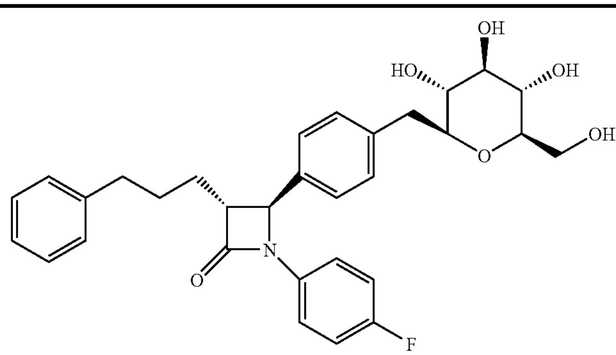 | 74-75 | |
| 12 | 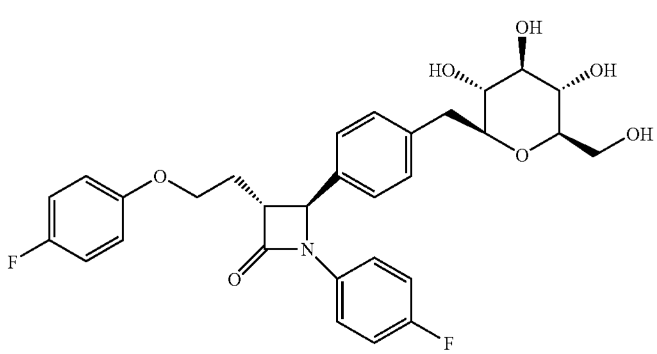 | 65-67 | (C = 0.5, CHCl$_3$) |

TABLE 3-continued

| No. | Structure | mp (° C.) | $[\alpha]_D^{25}$/(C, Solv.) |
|---|---|---|---|
| 13 | 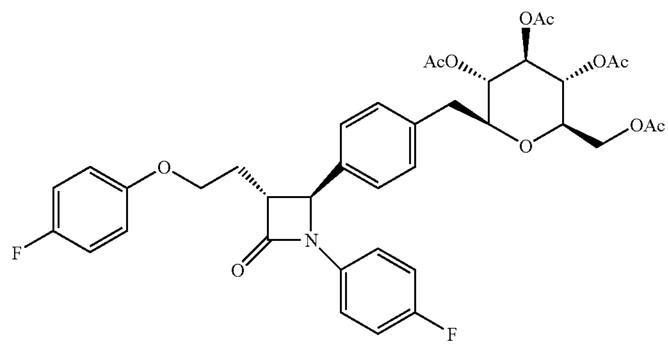 | 64-66 | |
| 14 | 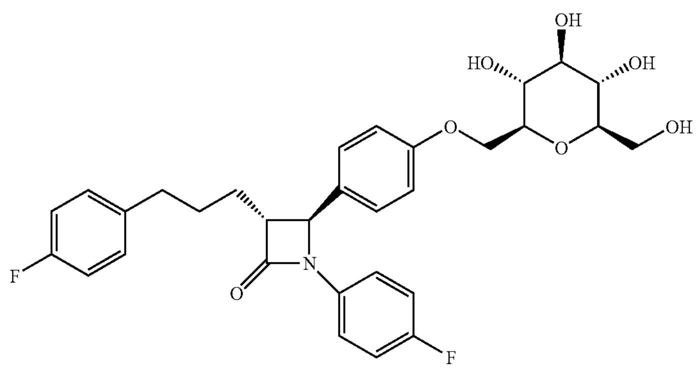 | 61-62 | |
| 15 | 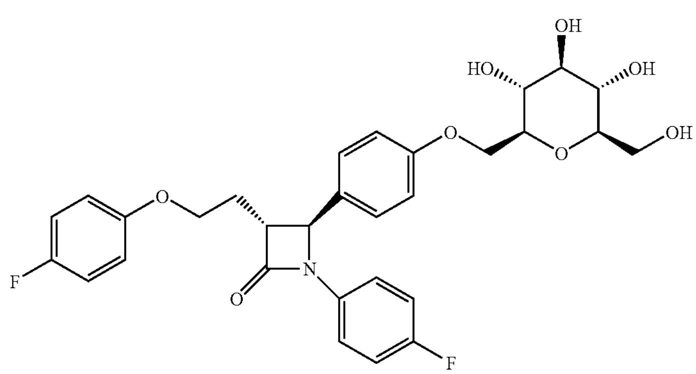 | 64-65 | |

TABLE 4

| No. | Structure | mp (° C.) | $[\alpha]_D^{25}$/(C, Solv.) |
|---|---|---|---|
| 16 | 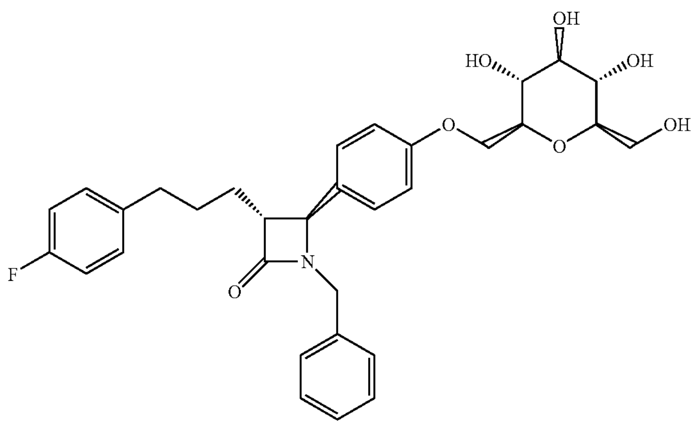 | 73-75 | |
| 17 | 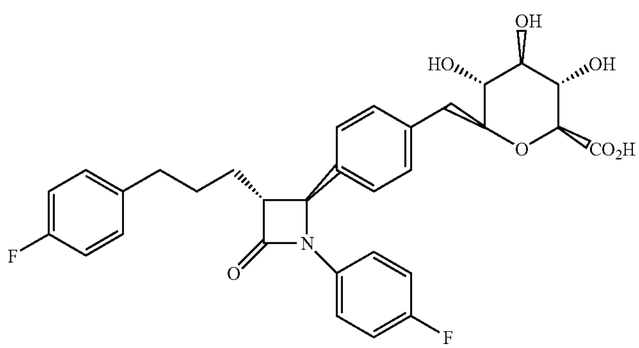 | 105-106 | |
| 18 | 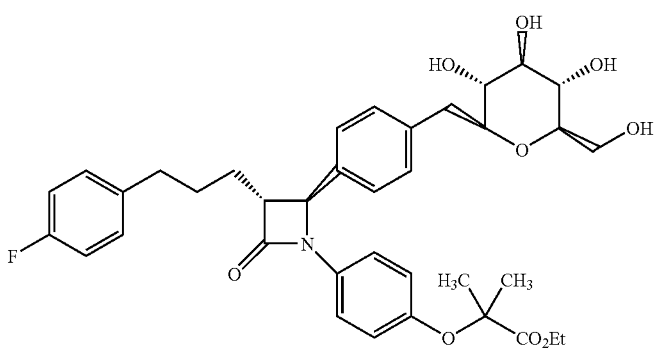 | 73-74 | |
| 19 | 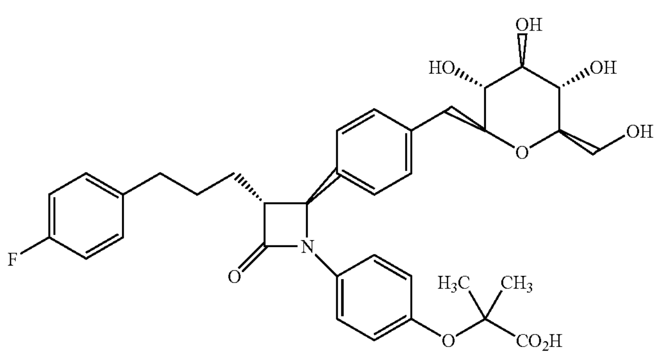 | 170-172 | |

TABLE 4-continued

| No. | Structure | mp (° C.) | $[\alpha]_D^{25}$/(C, Solv.) |
|---|---|---|---|
| 20 | 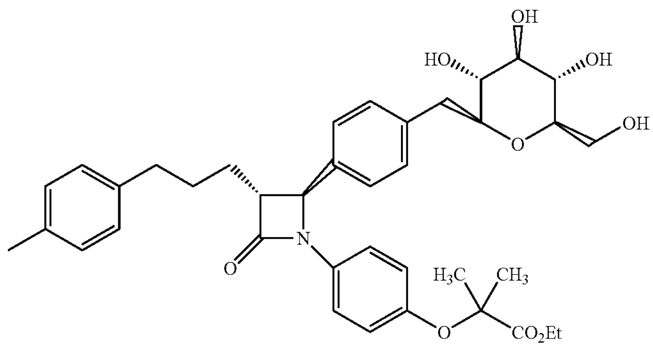 | 76-78 | |

TABLE 5

| No. | Structure | mp (° C.) | $[\alpha]_D^{25}$/(C, Solv.) |
|---|---|---|---|
| 21 | 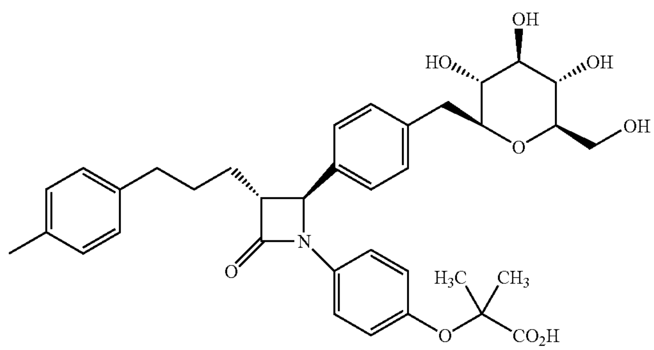 | 161-162 | |
| 22 | 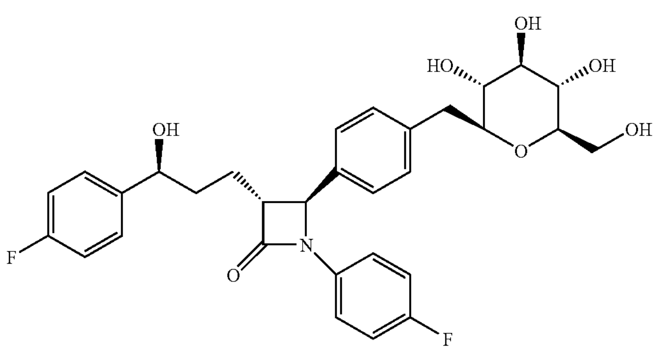 | 115-117 | −71.3 (C = 0.3, MeOH) |
| 23 | 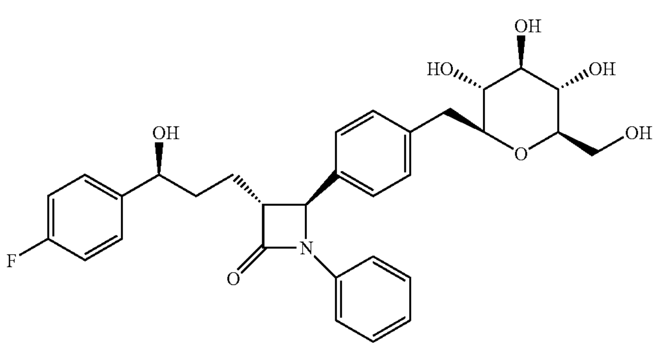 | 104-106 | −110 (C = 0.5, MeOH) |

TABLE 5-continued

| No. | Structure | mp (° C.) | $[\alpha]_D^{25}$/(C, Solv.) |
|---|---|---|---|
| 24 | 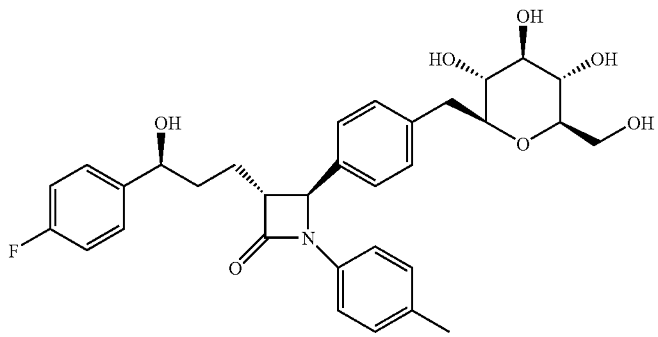 | 102-104 | −58.0 (C = 0.3, MeOH) |
| 25 | 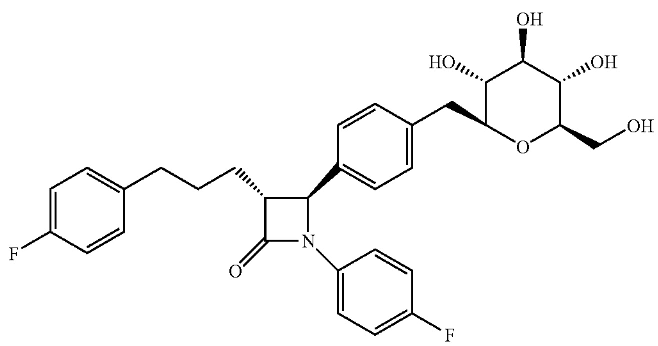 | 67-69 | −62.8 (C = 0.5, MeOH) |

TABLE 6

| No. | Structure | mp (° C.) | $[\alpha]_D^{25}$/(C, Solv.) |
|---|---|---|---|
| 26 | 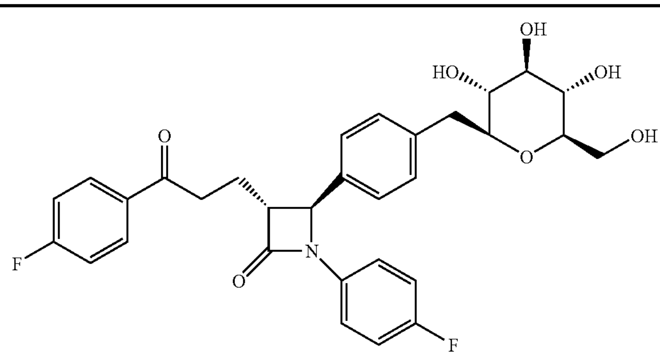 | 78-80 | −67.2 (C = 0.5, MeOH) |
| 27 | 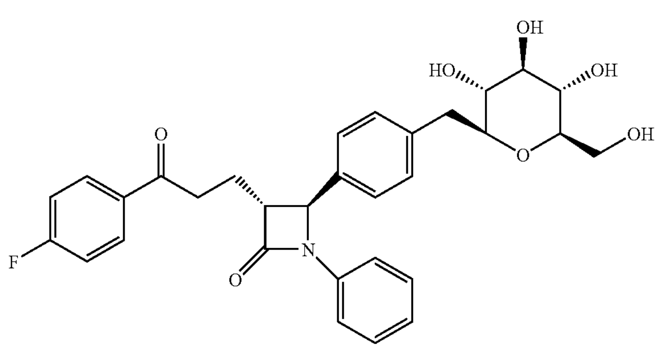 | 104-106 | −26.0 (C = 0.5, MeOH) |

TABLE 6-continued

| No. | Structure | mp (° C.) | $[\alpha]_D^{25}$/(C, Solv.) |
|---|---|---|---|
| 28 | 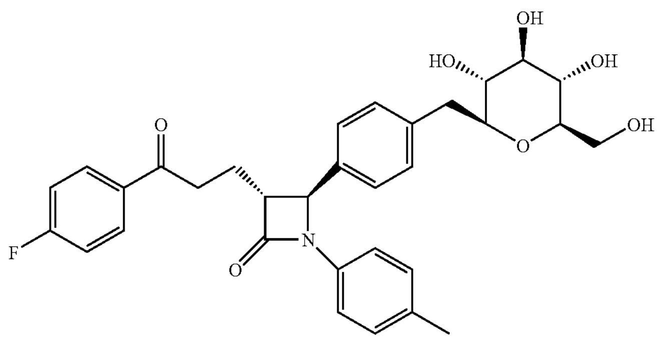 | 86-88 | -35.7 (C = 0.6, MeOH) |
| 29 | 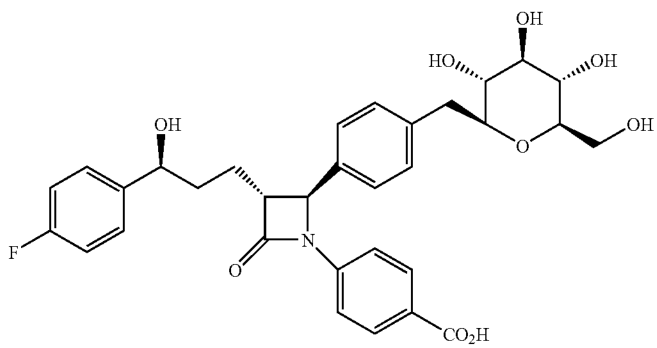 | 148-150 | -122.0 (C = 0.3, MeOH) |
| 30 | 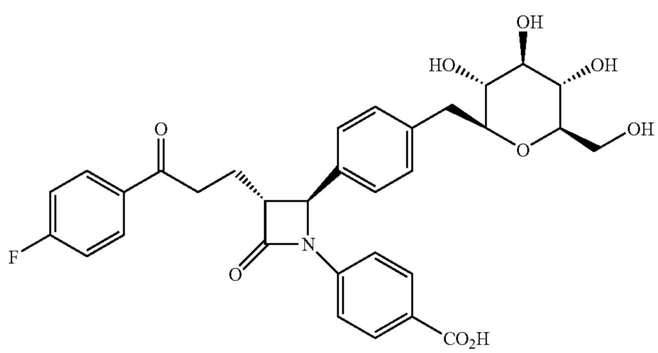 | 102-104 | -52.0 (C = 0.3, MeOH) |

TABLE 7

| No. | Structure | mp (° C.) | $[\alpha]_D^{25}$/(C, Solv.) |
|---|---|---|---|
| 31 | 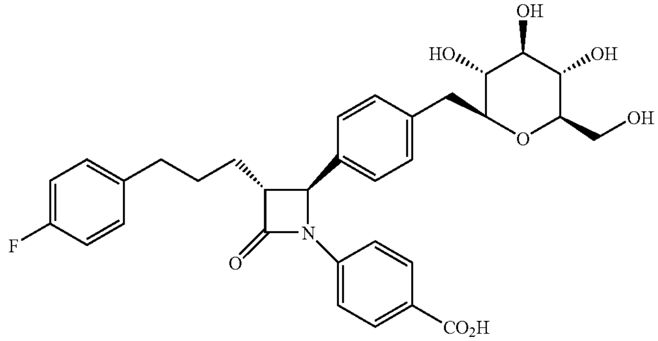 | 97-99 | |

TABLE 7-continued

| No. | Structure | mp (° C.) | $[\alpha]_D^{25}$/(C, Solv.) |
|---|---|---|---|
| 32 | 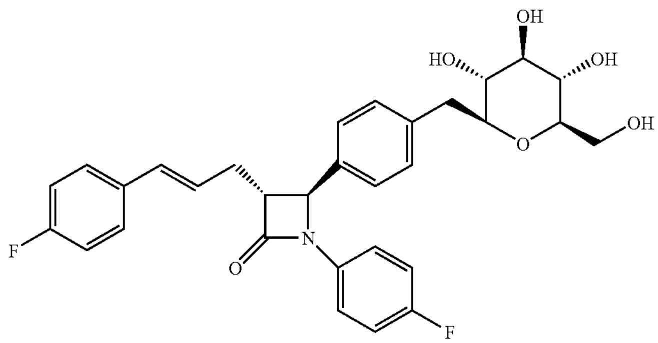 | liq | −39.3 (C = 0.8, MeOH) |
| 33 | 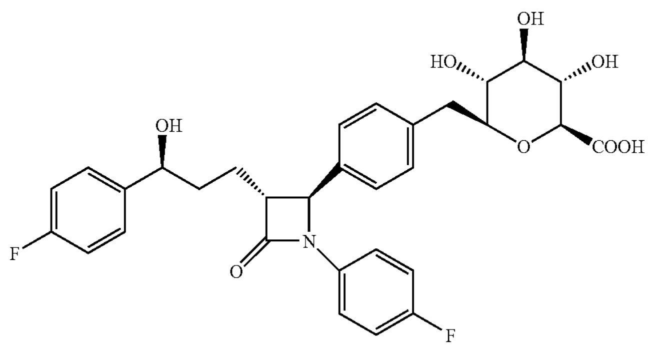 | 82-84 | −47.6 (C = 0.5, MeOH) |
| 34 | 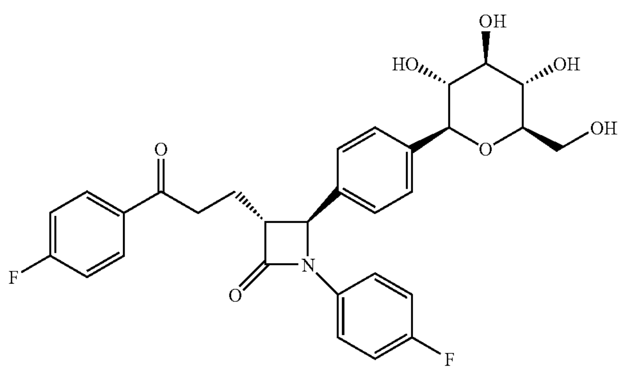 | 83-85 | |
| 35 | 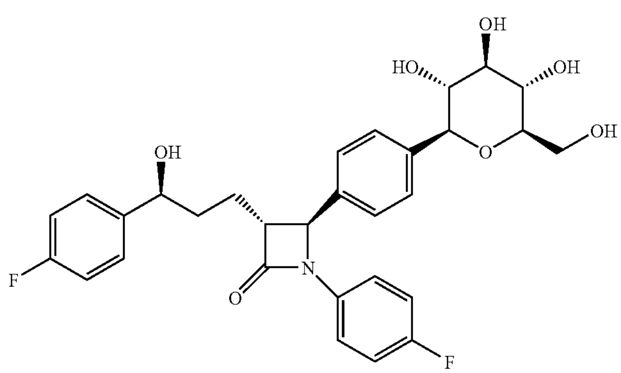 | 81-83 | |

TABLE 8

| No. | Structure | mp (° C.) | $[\alpha]_D^{25}$/(C, Solv.) |
|---|---|---|---|
| 36 | 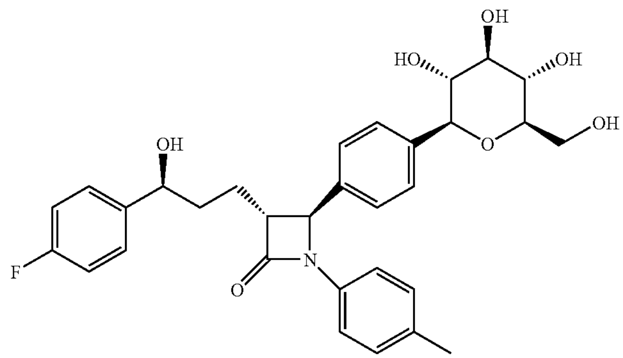 | 79-81 | |
| 37 | 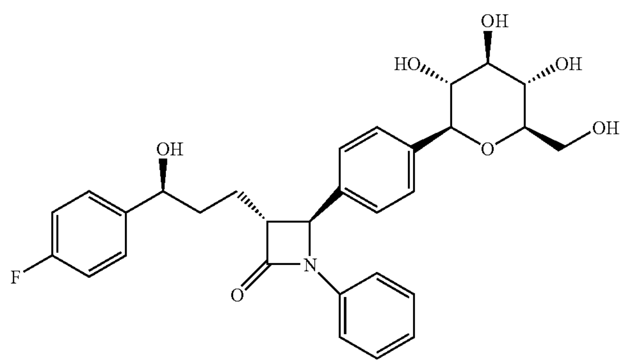 | 80-82 | |
| 38 | 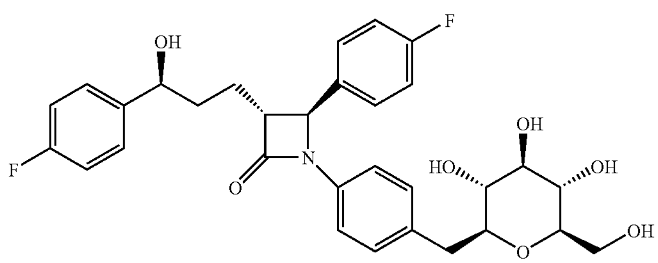 | 200-201 | −69.3 (C = 0.3, MeOH) |
| 39 | 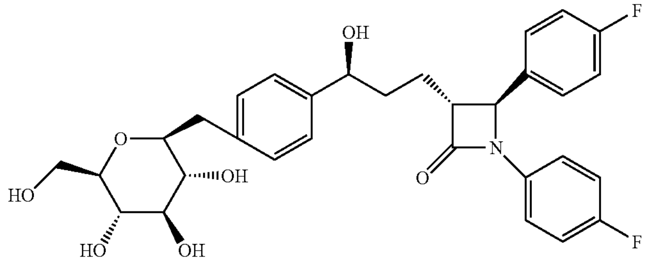 | 126-128 | −42.66 (C = 0.3, MeOH) |

TABLE 8-continued

| No. | Structure | mp (° C.) | $[\alpha]_D^{25}$/(C, Solv.) |
|---|---|---|---|
| 40 | 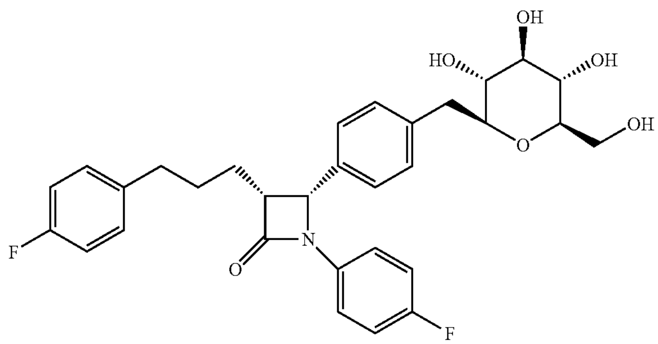 | 78-80 | |

TABLE 9

| No. | Structure | mp (° C.) | $[\alpha]_D^{25}$/(C, Solv.) |
|---|---|---|---|
| 41 | 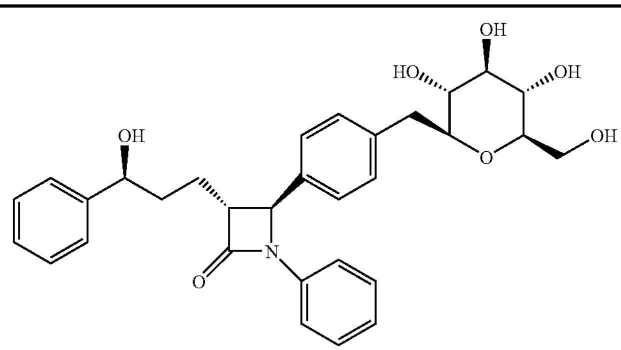 | 110-112 | −67.2 (C = 0.5, MeOH) |
| 42 | 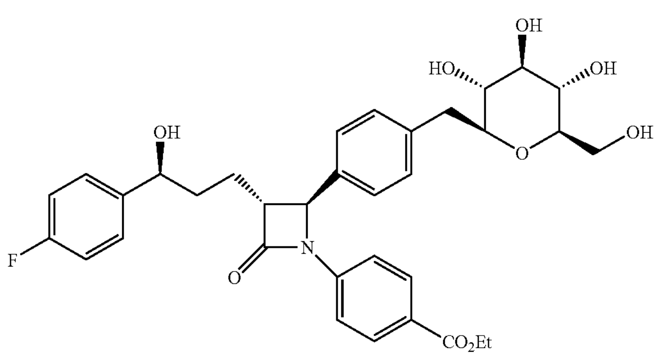 | 56-58 | −92.0 (C = 0.3, MeOH) |
| 43 | 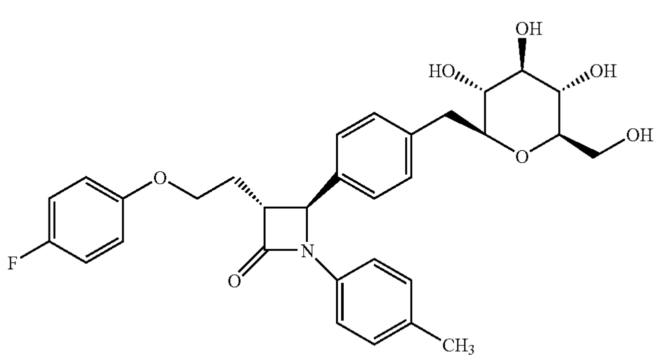 | 96-98 | −40.4 (C = 0.5, CHCl$_3$) |

TABLE 9-continued

| No. | Structure | mp (° C.) | $[\alpha]_D^{25}$/(C, Solv.) |
|---|---|---|---|
| 44 | 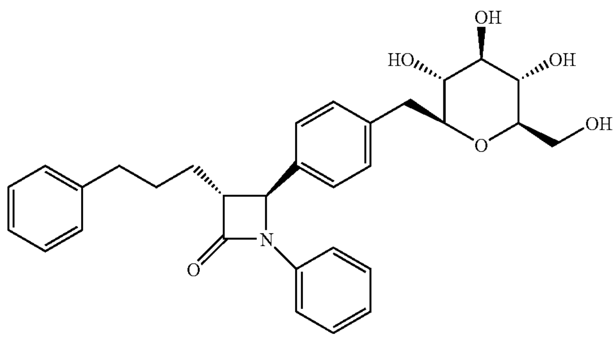 | 84-86 | −41.3 (C = 0.3, MeOH) |
| 45 | 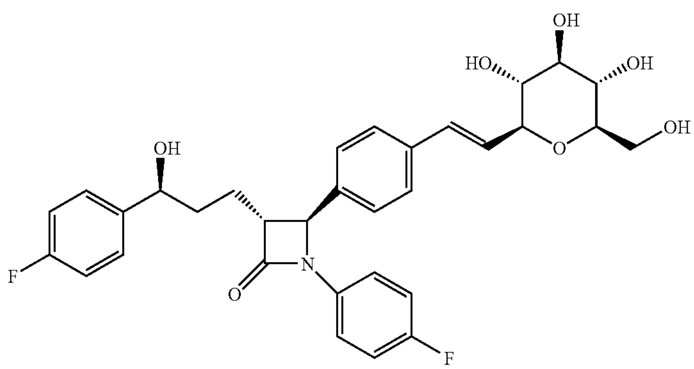 | 84-86 | −64.0 (C = 0.25, MeOH) |

TABLE 10

| No. | Structure | mp (° C.) | $[\alpha]_D^{25}$/(C, Solv.) |
|---|---|---|---|
| 46 | 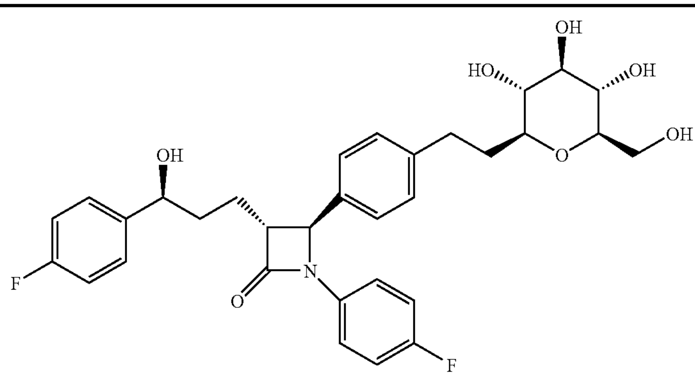 | 153-155 | −54.66 (C = 0.25, MeOH) |
| 47 | 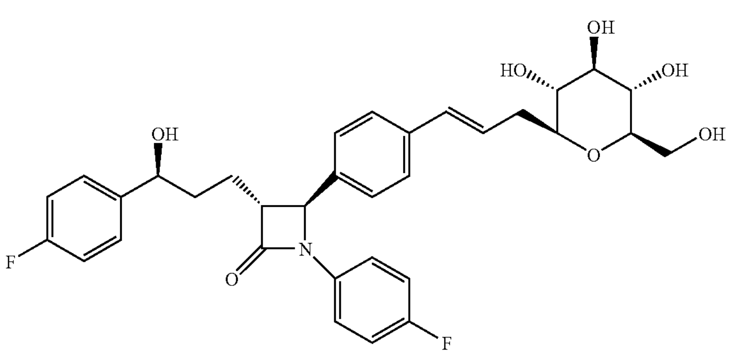 | 72-74 | −33.6 (C = 1.0, MeOH) |

TABLE 10-continued

| No. | Structure | mp (° C.) | $[\alpha]_D^{25}$/(C, Solv.) |
|---|---|---|---|
| 48 | 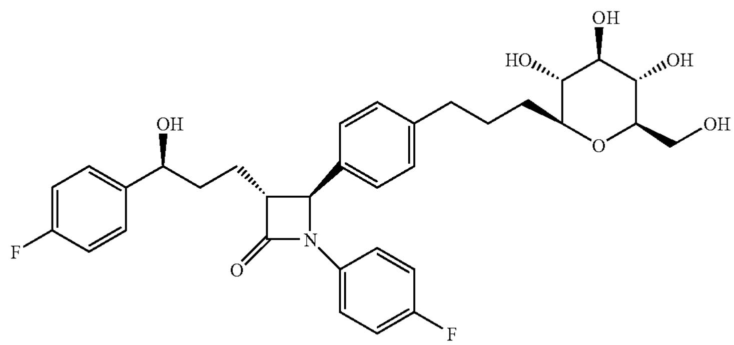 | 81-83 | −21.8 (C = 1.0, MeOH) |
| 49 | 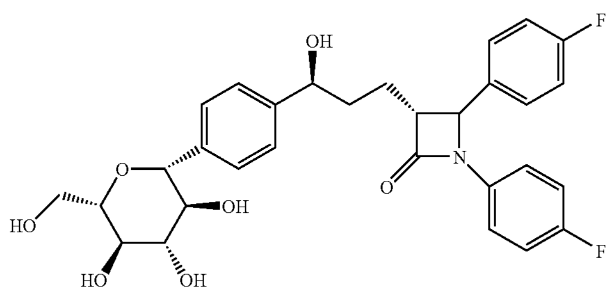 | 111-113 | −20.0 (C = 0.35, MeOH) |
| 50 | 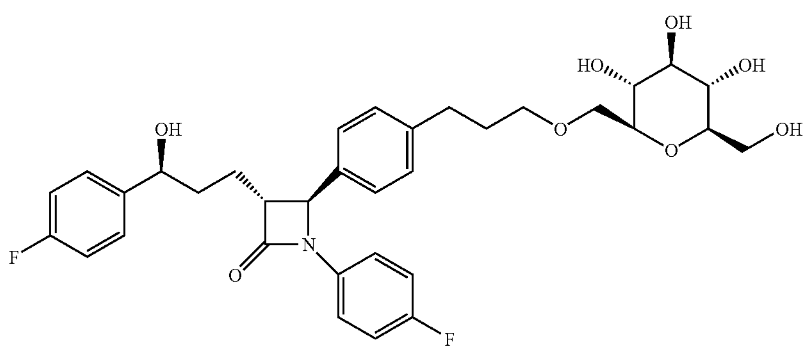 | 61-63 | −48.6 (C = 0.14, MeOH) |

TABLE 11

| No. | Structure | mp (° C.) | $[\alpha]_D^{25}$/(C, Solv.) |
|---|---|---|---|
| 51 | 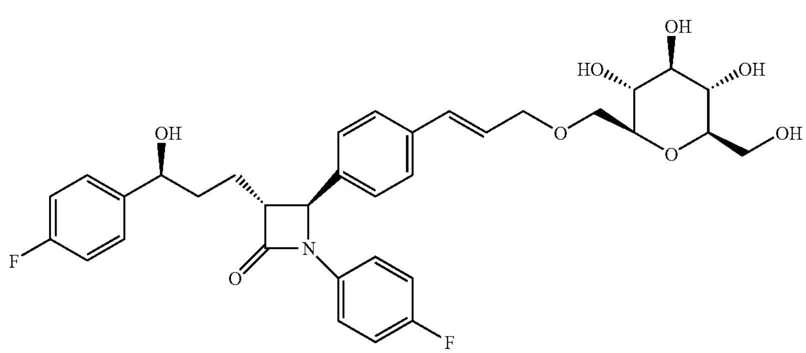 | 65–67 | −42.8 (C = 0.25, MeOH) |

TABLE 11-continued

| No. | Structure | mp (° C.) | $[\alpha]_D^{25}$/(C, Solv.) |
|---|---|---|---|
| 52 | 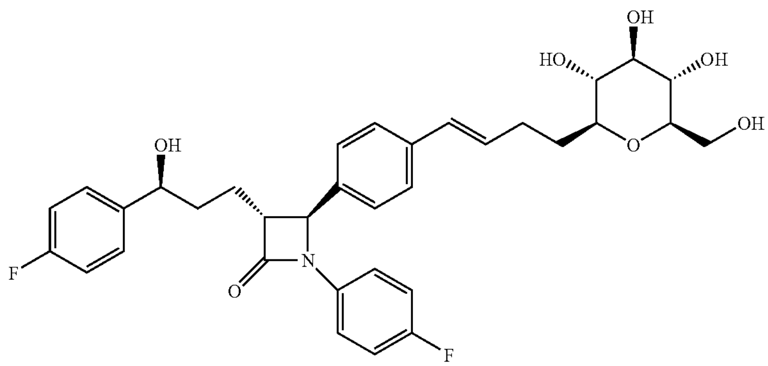 | 79–81 | −33.2 (C = 1.0, MeOH) |
| 53 | 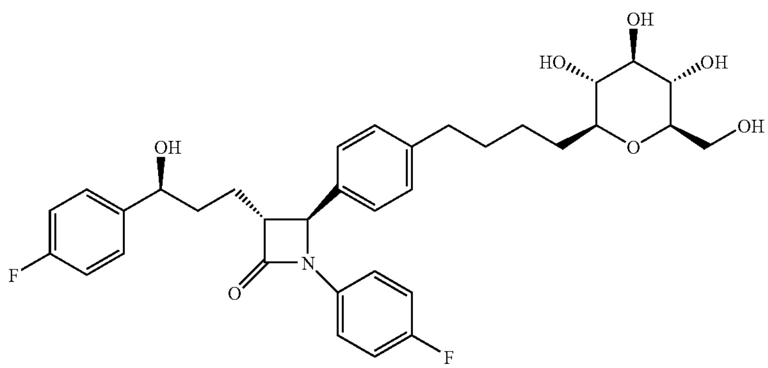 | 81–83 | −29.4 (C = 0.5, MeOH) |
| 54 | 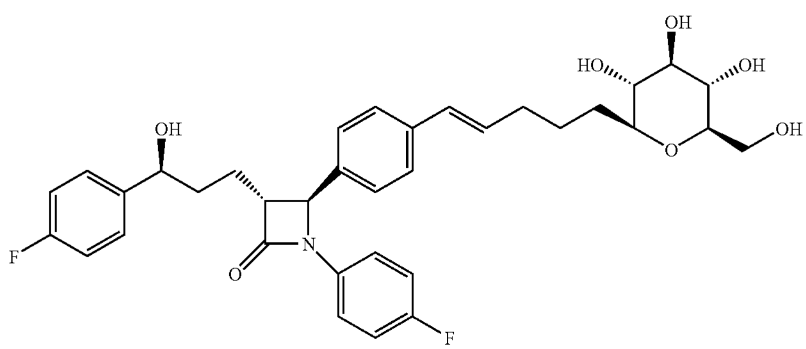 | 69–71 | −38.6 (C = 0.35, MeOH) |
| 55 | 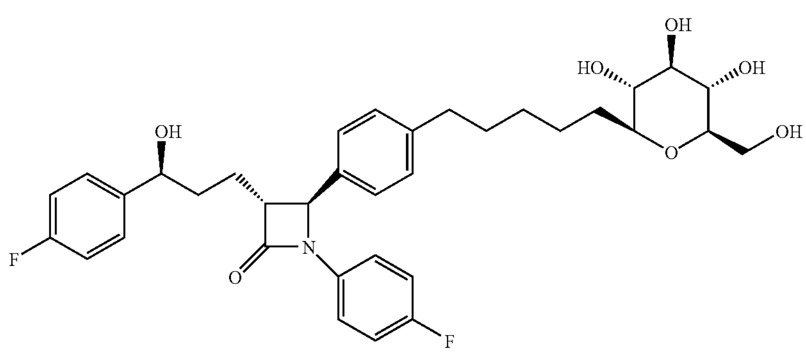 | 66–68 | −42.9 (C = 0.35, MeOH) |

TABLE 12

| No. | Structure | mp (° C.) | $[\alpha]_D^{25}$/(C, Solv.) |
|-----|-----------|-----------|------------------------------|
| 56 | 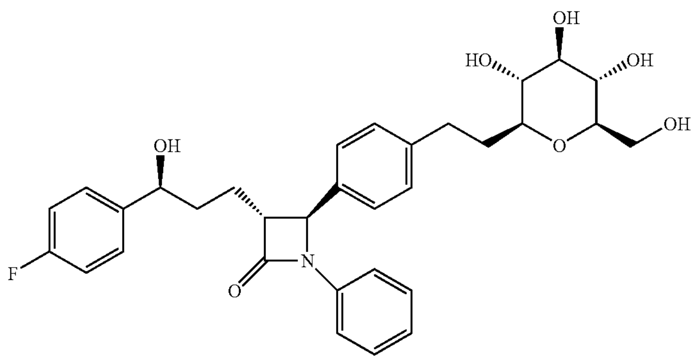 | 82–84 | −49.2 (C = 1.0, MeOH) |
| 57 | 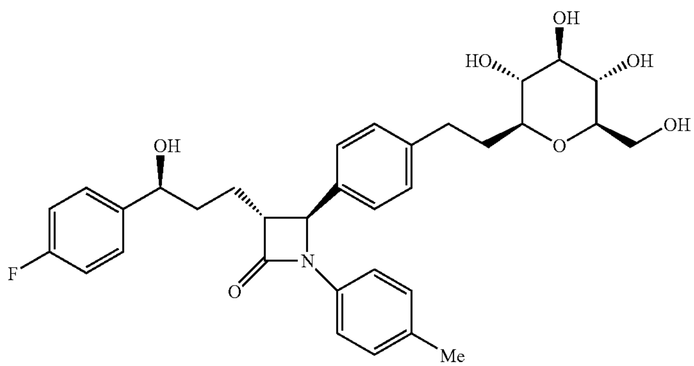 | 116–118 | −76.0 (C = 0.3, MeOH) |
| 58 | 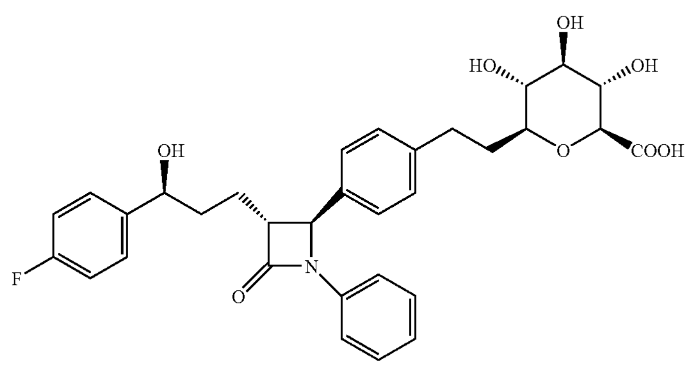 | 110–112 | −40.3 (C = 0.7, MeOH) |

Also, cholesterol biosynthesis inhibitors using in the present invention is at least one sort chosen from the group consisit of HMG-CoA reductase inhibitors, squalene synthase inhibitors and squalene epoxydase inhibitors. HMG-CoA reductase inhibitors include, for example, pravastatin, lovastatin, fluvastatin, simvastatin, itavastatin, atorvastatin, cerivastatin, rosuvastatin, pitavastatin and carvastatin (TF802); squalene synthase inhibitors include, for example, squalestatin 1; squalen epoxydase inhibitors include, for example, NB-598 ((E)-N-ethyl-N-(6,6-dimethyl-2-heptyn-4-ynyl)-3-[(3,3'-bithiophen-5-yl) methoxy]benzenemethanamine hydrochloride). One or over two agents chosen from those are used in the present invention.

Also, fibrate-type cholesterol lowering agents using in the present invention is at least one sort chosen from the group consisting of clofibrate, bezafibrate, cinfibrate, fenofibrate, gemfibrogyl and AHL-157.

The medicine in the present invention is administered in oral dosage or non-oral dosage form. And, combined usage of a compound represented by the general formula (I) or pharmaceutical acceptable salts and cholesterol biosynthesis inhibitors and/or fibrate-type cholesterol lowering agents can be carried out in various forms. For example, a compound represented by the general formula (I) or pharmaceutical acceptable salts and cholesterol biosynthesis inhibitors and/or fibrate-type cholesterol lowering agents are mixtured at the predetermined ratio, furthermore, it is able to form a combination agent which blended additives and excipients according to the request (a powder agent, a tablet, a granule agent, a capsule agent, a liquid agent, a suspended agent, a suppository, an ointment agent, an inhalation agent and others). Additives and excipients are lubricants, binders, collapses, fillers, buffers, emulsifiers, preservatives, anti-oxidants, coloring agents, coating agents, suspending agents and others.

Also, it is able to form a kit by single packaging a container containing a compound represented by the general formula (I) or pharmaceutical acceptable salts and a container containing cholesterol biosynthesis inhibitors and/or fibrate-type cholesterol lowering agents. Also, it is able to administer a compound represented by the general formula (I) or pharmaceutical acceptable salts and cholesterol biosynthesis inhibitors and/or fibrate-type cholesterol lowering agents simultaneously or consecutively.

The daily dose of the medicine in the present invention is determined by the potency of the compound administered, the weight, age, and condition of the patient and others. Also, the medicine is administered in a single dose or 2~5 divided doses depending oral dosage or non-oral dosage forms. A compound represented by the general formula (I) or pharmaceutical acceptable salts are administered the amount of 0.1~100 mg/kg (mammalian weight) per day in division. Cholesterol biosynthesis inhibitors are administered the amount of 1 mg~3 g/kg (mammalian weight) per day in division, and for HMG-CoA reductase inhibitors are administered the amount of 5~100 mg/kg (mammalian weight) per day in division. For fibrate-type cholesterol lowering agents are administered the amount of 1~1000 mg/kg (mammalian weight) per day in division.

EXAMPLE

In the pharmacological experiments of this example, the compound of compound No. 56 (called compound 56 as following) and the compound of compound No. 37 (called compound 37 as following) in the above Table were used as a compound represented by the general formula (I) or pharmaceutical acceptable salts.

Pharmacological Experiment 1

The pharmacological experiment of serum cholesterol lowering action by the combination of compound 56 and atorvastatin or fenofibrate in cholesterol-fed rat.

Male Splague-Dawley rats weighing 300~500 g (Nihon SLC Co. Ltd.) were fed MF-2 chow (Nihon Crea Co. Ltd.) until study onset. At the study onset, the chow was changed to MF-2 chow containing 1% cholesterol and 0.5% cholic acid. Compound 56 at 0.3 mg/kg, atorvastatin at 1 mg/kg or fenofibrate at 10 mg/kg dissolved in polyethylene glycol 400 were simultaneously administered once a day for 7 days. Twenty hours after the last administration, blood was collected from the abdominal aorta under ether anaesthesia, and serum was separated. The cholesterol value was measured using Cholesterol E Test Wako (Wako Pure Chemical Co. Ltd.). Furthermore, the effect of combined dosage of compound 56 at 0.3 mg/kg and atorvastatin at 1 mg/kg or fenofibrate at 10 mg/kg were examined similarly. The results were shown in Table 13. The experimental No. of 1~3, 4 and 5 indicates the case of compound 56 alone, atrovastatin alone and fenofibrate alone, respectively. The experimental 5 and 6 indicates the combined dosage examples in the present invention. Each reduction percent is shown as the value to control.

TABLE 13

| Experimental No. | Group | Dose (mg/kg/day) | Number per group | Reduction % of serum cholesterol value |
|---|---|---|---|---|
| 1 | Compound 56 | 0.03 | 6 | 1.9 |
| 2 | Compound 56 | 0.3 | 6 | 6.9 |
| 3 | Compound 56 | 1 | 6 | 33.5 |
| 4 | Atorvastatin | 1 | 6 | 6.2 |
| 5 | Fenofibrate | 10 | 6 | 10.7 |
| 6 | Compound 56 Atorvastatin | 0.3 1 | 6 | 20.2 |
| 7 | Compound 56 Fenofibrate | 0.3 10 | 6 | 41.3 |

From Table 13, in the case of combined dosage compound 56 at 0.3 mg/kg/day and atrovastatin 1 mg/kg/day (Experimental No. 6), and compound 56 at 0.3 mg/kg/day and fenofibrate at 10 mg/kg/day (Experimental No. 7), each reduction % of serum cholesterol value was over the sum of reduction % when each agent was administered alone (Experimental No. 2, 4 and 5), indicating synergistic effect.

Pharmacological Experiment 2

Except of the use of compound 37 instead of compound 56, quietly same experiment to pharmacological experiment 1 was carried out. The results were shown in Table 14. Each reduction % is shown as the value to control.

TABLE 14

| Experimental No. | Group | Dose (mg/kg/day) | Number per group | Reduction % of serum cholesterol value |
|---|---|---|---|---|
| 11 | Compound 37 | 0.03 | 6 | 5.6 |
| 12 | Compound 37 | 0.3 | 6 | 18.0 |
| 13 | Compound 37 | 1 | 6 | 31.0 |
| 14 | Atorvastatin | 1 | 6 | 6.2 |
| 15 | Fenofibrate | 10 | 6 | 10.7 |
| 16 | Compound 37 Atorvastatin | 0.3 1 | 6 | 31.5 |
| 17 | Compound 37 Fenofibrate | 0.3 10 | 6 | 39.5 |

From Table 14, in the case of combined dosage compound 37 at 0.3 mg/kg/day and atorvastatin 1 mg/kg/day (Experimental No. 16), and compound 37 at 0.3 mg/kg/day and fenofibrate at 10 mg/kg/day (Experimental No. 17), the reduction % of serum cholesterol values were over the sum of reduction % when each agent was administered alone (Experimental No. 12, 14 and 15), indicating synergistic effect.

INDUSTRIAL APPLICABILITY

The medicine consist of the combination of a compound represented by the following general formula (I) or pharmaceutical acceptable salts and cholesterol biosynthesis inhibitors and/or fibrate-type cholesterol lowering agents show the synergistic effect and an excellent serum cholesterol lowering effect or preventive or therapeutic effect for atherosclerosis. Therefore, it is useful for serum cholesterolol lowering or preventive or therapy for atherosclerosis.

The invention claimed is:

1. A serum cholesterol lowering agent or preventive or therapeutic agent for atherosclerosis comprising a combination of a compound represented by the following formula or its pharmaceutically acceptable salts

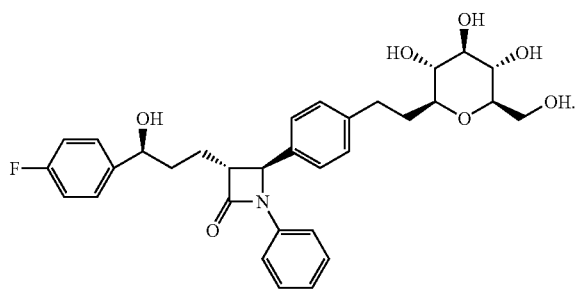

and at least one HMG-CoA reductase inhibitor selected from the group consisting of atorvastatin and rosuvastatin.

2. The serum cholesterol lowering agent or preventive or therapeutic agent for atherosclerosis according to claim 1 in the form of a powder, tablet, granule, capsule, liquid, suspension, suppository, ointment or inhalant.

3. The serum cholesterol lowering agent or preventive or therapeutic agent for atherosclerosis according to claim 1 further comprising one or more pharmaceutically acceptable additives or excipients selected from lubricants, binders, collapses, fillers, buffers, emulsifiers, preservatives, anti-oxidants, coloring agents, coating agents or suspending agents.

4. The serum cholesterol lowering agent or preventive or therapeutic agent for atherosclerosis according to claim 1 comprising the compound represented by the formula

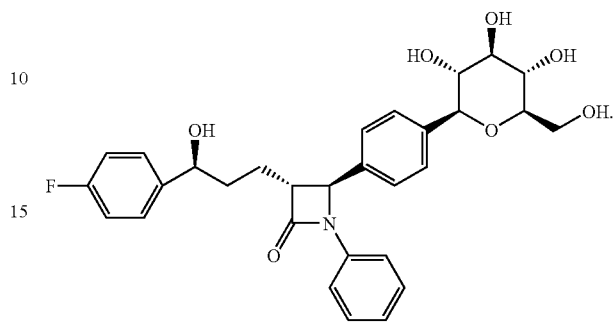

in amounts corresponding to 0.1~100 mg/kg (mammalian weight) per day in divisions and the HMG-CoA reductase inhibitor in amounts corresponding to 5~100 mg/kg (mammalian weight) per day in divisions.

* * * * *